(12) United States Patent
Pan

(10) Patent No.: US 8,205,622 B2
(45) Date of Patent: Jun. 26, 2012

(54) ELECTRONIC CIGARETTE

(76) Inventor: Guocheng Pan, Cupertino, CA (US)

( * ) Notice: Subject to any disclaimer, the term of this patent is extended or adjusted under 35 U.S.C. 154(b) by 435 days.

(21) Appl. No.: 12/437,511

(22) Filed: May 7, 2009

(65) Prior Publication Data

US 2010/0242974 A1    Sep. 30, 2010

(30) Foreign Application Priority Data

Mar. 24, 2009   (CN) .......................... 2009 1 0080147

(51) Int. Cl.
*A24F 47/00* (2006.01)
(52) U.S. Cl. ...................................................... 131/273
(58) Field of Classification Search .................... 131/273
See application file for complete search history.

(56) References Cited

U.S. PATENT DOCUMENTS

| | | | | |
|---|---|---|---|---|
| 5,060,671 | A | * | 10/1991 | Counts et al. .................. 131/329 |
| 2008/0092912 | A1 | * | 4/2008 | Robinson et al. ............. 131/200 |
| 2009/0283103 | A1 | * | 11/2009 | Nielsen et al. ................ 131/273 |

FOREIGN PATENT DOCUMENTS

| | | |
|---|---|---|
| CN | 201067728 Y | 6/2008 |
| CN | 201238610 Y | 5/2009 |
| CN | 201379073 Y | 1/2010 |
| EP | 0845220 A1 | 6/1998 |
| EP | 845220 A1 * | 6/1998 |
| WO | WO 2009/152651 A1 | 12/2009 |

OTHER PUBLICATIONS

UK Intellectual Property Office, "Combined Search and Examination Report" for Application No. GB0913768.8, report dated Apr. 8, 2010 (5 pages).

* cited by examiner

*Primary Examiner* — Matthew Daniels
*Assistant Examiner* — Cynthia Szewczyk
(74) *Attorney, Agent, or Firm* — Squire Sanders (US) LLP

(57) ABSTRACT

An electronic cigarette has two tubes that resemble a cigarette: an electronic inhaler and an electronic atomizer. The two tubes are connected through one or more electric connectors to form an electronic cigarette. Inside the inhaler is a rechargeable or non-rechargeable power source such as a battery, which supplies electric power to the electronic inhaler and atomizer and ensures that both work together like a cigarette. In addition to the power source, the inhaler also includes other major components: an electric airflow sensor to detect air movement generated by a user's inhaling or puffing act and a Single Chip Micyoco which controls the atomization process. The sensor's role is to collect an airflow signal that triggers the Single Chip Micyoco, which in turn instructs the electronic cigarette to supply electric power to the inhaler and atomizer connected through an electric connector. Inside the electronic atomizer are an electric connector, electric heating wire, liquid container, and atomizer cap with an air-puffing hole. The user inhales through the air-puffing hole at an end of the electronic cigarette to create an air inflow, which triggers the atomization process. The Single Chip Micyoco driven by a software program controls the electronic cigarette in an on/off manner according to the signal detected by the electric sensor on the airflow and completes a cycle of atomization, which converts a solution of a liquid form inside the liquid container to a gas form. This entire process achieves the emulated smoking process of a user, who is satisfied with scent taste that mimics cigarette smoking.

18 Claims, 7 Drawing Sheets

ELECTRONIC CIGARETTE

This application claims the priority of Chinese Patent Application No. 200910080147.5, filed Mar. 24, 2009, the entire disclosure of which is incorporated herein by reference.

TECHNICAL FIELD

The present invention relates to an electronic cigarette.

BACKGROUND OF THE INVENTION

Tobacco smoking creates one of the most serious health threats to the mankind. Although people have used tobacco for centuries, cigarettes did not appear in the mass-manufactured form until the 19th century. Today, the number of smokers has grown to over 1.3 billion worldwide. In the high-income countries, smoking has been in overall decline for decades, although it continues to rise in some groups. In low- and middle-income countries, by contrast, cigarette consumption has been increasing. Death directly related to the use of tobacco is estimated to be at least 5 million people annually. If every tobacco user smoked one pack a day, there would be a total of 1.3 billion packs of cigarettes smoked each day, emitting a large amount of harmful tar, CO and other more than 400 gas contents to homes and offices, causing significant second-hand smoking damages to human health.

Nicotine is highly addictive. Tar in cigarettes increases smoker's risk of lung cancer, emphysema, and bronchial disorders. The carbon monoxide in smoke increases the chance of cardiovascular diseases. Secondhand smoke causes lung cancer in adults and greatly increases the risk of respiratory illnesses in children. It is hard to quit smoking. In order to overcome these problems, people have invented many new technologies and products, such as nicotine patches, nicotine gum, etc. Recently, several new inventions have been made, including a Japanese patent (#3-232481), which proposes a simulated cigarette device with an insulated tube, inside which a heated generator and solid scent media are stored. Through an electric power source, the heat generator supplies heat to the scent media to generate an odor which is then absorbed to ease smokers' need for cigarette smoking. However, this simulated cigarette device requires a long time to reach a temperature high enough to generate the scent odor for users. Hence, this tool does not meet smokers' need.

A Chinese patent (#03111582.9) proposes a non-flammable atomizing electronic cigarette, which is intended to be a smoking cessation device and a replacement for conventional cigarettes. This product includes a shell, battery, high-frequency generator, nicotine-fluid chamber, controlling circuit, display screen, electronic inductor, body-contact transducer, piezoelectricity supersonic atomizer, and high-temperature air emitter. It also includes an electrically-controlled pump, metering valve, unidirectional injection valve, etc. Due to its extreme complexity in structure and very high manufacturing cost, this kind of electronic cigarettes is difficult to commercialize.

Another Chinese patent (#ZL200410048792.6) proposes an electronic cigarette, which has a stick-like shell, air-puffing hole, emitting device, pressure-modifying driver, control device, detection device, and smoke generator. This invention uses the control device to drive the emitting device to eject liquid drops generated from scent media outside of the shell. This invention also contains an atomizing device inside the shell, which vaporizes the liquid drops into vapor mists to be inhaled by the user by puffing through the smoke-flow hole at an end of the shell. This inhaling allows the user to absorb the scent-media in a vapor form together with the airflow inside the shell. In this way, the user is satisfied with a scent taste that mimics cigarette smoking.

In sum, the existing electronic cigarette devices have several major drawbacks: (1) too complex to be implemented as an ordinary consuming product and too costly for manufacturing and maintenance; (2) all having problems such as fluid leaking, reversal, nicotine-liquid exposing, discontinuous vaporizing, hard inhaling, and sub-standard sanitation; (3) all using mechanical devices as an airflow detector, which has a short life and is too sensitive to outside temperature and humidity changes.

SUMMARY OF THE INVENTION

An electronic cigarette described and claimed in this patent application overcomes at least some of the above-described problems associated with the prior art.

An object of this invention is to provide a green alternative to harmful, polluting conventional cigarettes and to overcome at least some of the above-described problems associated with prior electronic cigarettes.

This invention adopts a brand new technical solution to create a device that highly resembles a conventional cigarette and the cigarette smoking process. An electronic cigarette of the present invention preferably is comprised of two parts, one being an electronic inhaler and the other being an integrated electronic atomizer. Each part may have a metal or plastic tube, and the two tubes may have an identical or similar diameter. The inhaler preferably includes one or more of an electric power source, electric sensor, single chip micyoco, and LED indicator. The electric power source, which can be a rechargeable or non-rechargeable battery, supplies electricity to the atomizer to vaporize a liquid inside an atomizer chamber. On the first end of the inhaler tube may be a cigarette cap with a small hole for airflow. On the second end of the tube may be an electric connector with either outskirt screw thread or a DC socket.

The electronic atomizer may include a liquid-container or a chamber inside the atomizer tube, which preferably also includes a heat equalizer that has an electric heat wire, a supporting piece which holds up the heat equalizer, and an electric connector. On the first end of the atomizer tube may be a cap with an air-puffing hole for the user to draw an airflow and for the emission of vapor mist. On the second of the atomizer tube may be an electric connector with either internal screw thread or a DC plug.

In a preferred embodiment, the connection between the electronic inhaler and electronic atomizer through the connectors on both parts forms an entire electronic cigarette. When the user puffs on the electronic cigarette through the air-puffing hole on the first end of the atomizer, the electronic sensor detects an airflow and converts it to a signal, which then wakes up the single chip micyoco to record the signal. The single chip micyoco guided by its embedded software instructions may turn on the electric power source to supply an electricity current with a predefined time length. This electric current preferably flows through the electric heat wire inside the atomizer tube, which then heats up the heat equalizer with absorbed liquid from the liquid-container. The heated equalizer converts the liquid into a form of vapor mist, which is finally drawn into the month of the user. This completes an entire cycle of vaporizing process from which the user gets satisfaction of "smoking."

One of the unique technical advances in this invention is the integrated atomizer technology. Previous atomizing units are directly embedded into the inhaler tubes, while the liquid chamber is made as a separate piece, which must be inserted into the atomizing chamber before the electronic cigarette can be used. This old technology has several major drawbacks: (1) inconvenient in using the electronic cigarette, (2) insanitary and even unsafe to users due to the direct exposure of liquids, and (3) a short life for the atomizing unit. The integrated atomizer of the present invention is an integrated and disposable part, which overcomes some or all of the problems stated above. In addition, the integrated atomizer technology has also minimized the likelihood of a liquid leak, liquid reversal to the month when the user puffs on the electronic cigarette, and discontinuous vaporizing problems.

Another technical advance of the integrated atomizer is the material of the heat equalizer, which plays the key role in ensuring of large vapor volumes and the elimination of the disconnected vaporization problem. This material of the heat equalizer, which may be made of a non-toxic inorganic material, is required to withstand a high temperature up to 2000 degrees centigrade.

The electronic inhaler of the present invention represents the state-of-the-art electronic cigarette technology in both structural design and microelectronic devices. One of the new technologies that may be used with an electronic cigarette of the present invention is the use of an electric airflow sensor instead of a mechanical device in detecting an airflow generated by the user's puffing and creating a signal for the microprocessor to activate the electric circuit. Once the circuit is activated, the electric power source sends an electric current to the system and the connected integrated atomizer, and the vaporizing process begins. When the puffing stops, the microprocessor instructs the electric power source to stop supplying the electricity current, and the vaporizing process stops.

This new technology provides a solution to the problems of the current inhaling technology by eliminating aging and short-life drawbacks of the current mechanical device technology. Moreover, the new technology also makes the puffing of users on the cigarette much easier and smoother. It is more sensitive in turning on and off the vaporizing process than the conventional mechanical system. The life of an electric sensor can last for five years, many times longer than the mechanical device.

The new electronic inhaler may also adopt a new technology of a protection board, which protects the inhaler from damage of a short-circuit event. Since use of electric connectors between the inhaler and atomizing units, there is always a likelihood of a short-circuit, which usually destroys some of the electric components on the circuit board, and sometime even destroys the electric power source—the battery. Incorporation of the protection unit completely eliminates short-circuit problems, and extends the life of the electronic inhaler.

DETAILED DESCRIPTION OF PREFERRED EMBODIMENTS

Figure 1:
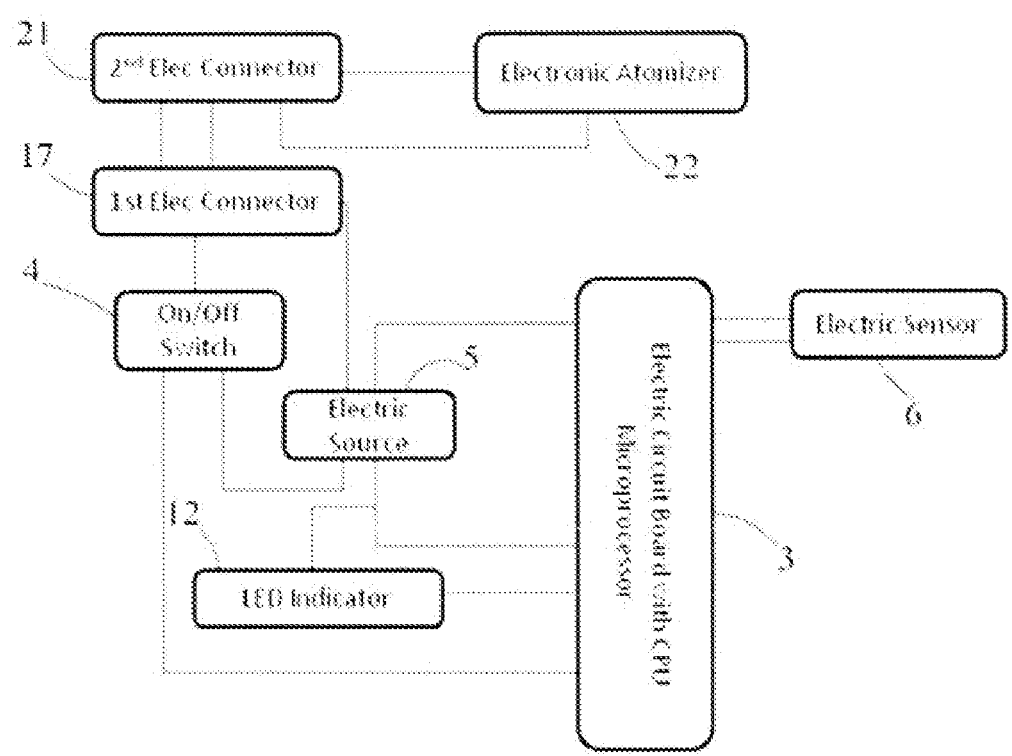
FIG. 1 illustrates an electric circuit structure of an embodiment of the present invention.

Referring to FIG. 1, the electric power source 5 supplies an electric current to the electronic atomizer 22 and other electric units to heat up the heat equalizer through the connected electronic inhaler and atomizer 22 through the first electric connector 17 of the inhaler and the second electric connector 21 of atomizer 22. The electric sensor 6 plays the role of detecting the airflow resulted from the puffing action of a user, and wakes up the single chip micyoco 3 to turn on the electricity on/off switch 4 and generate an electric current form the electric power source 5 to the electronic atomizer 22 for vaporizing of a liquid inside the liquid chamber inside the atomizer 22. The single chip micyoco 3 instructs the electric power source 5 to supply electricity to the system by its embedded computer programs when a signal is generated through the airflow detected by the electric sensor 6 from the user's puffing action.

The LED indicator 12, which is connected to both the CPU processor 3 and electric power source 5, lights up when the electric current flows and it is turned off when the electric current stops flowing. The magnitude of the electric current supplied from the electric power source 5 depends on the magnitude of signal detected from the airflow proportional to the strength of user's puffing action. This, in turn, controls the temperature and heat generated through the electric heating wire and heat equalizer. This process closely mimics the process of cigarette smoking.

Figure 2:
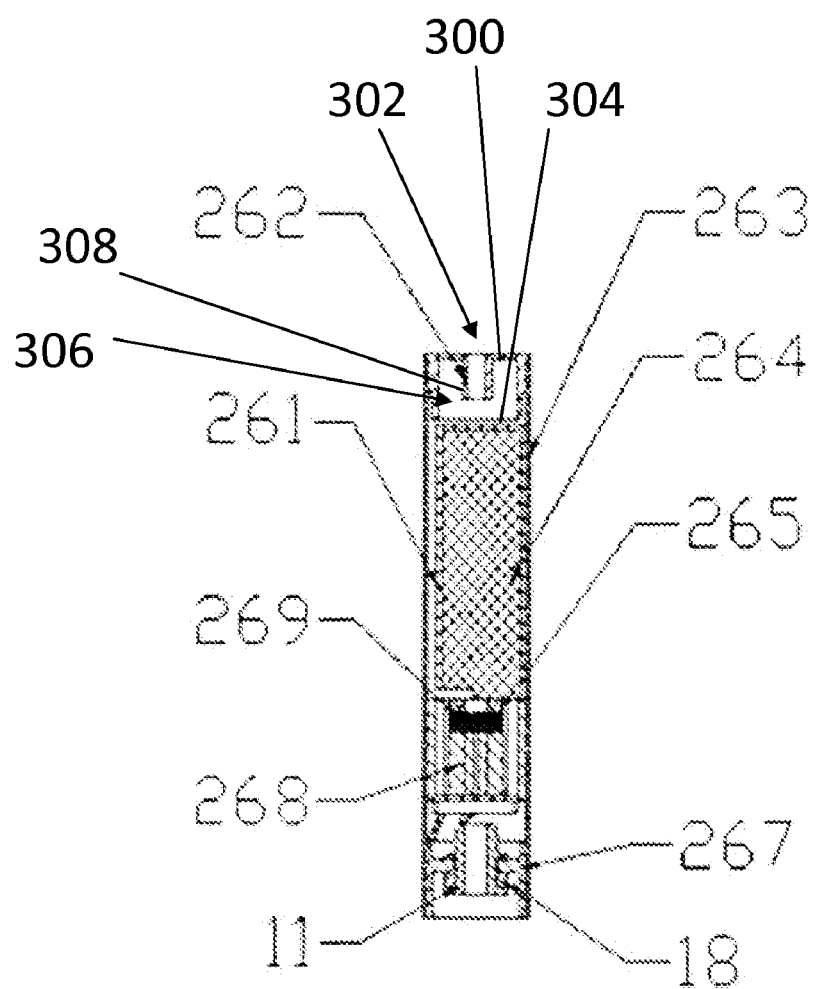
FIG. 2 is a section view of an integrated electronic atomizer of the present invention.

FIG. 2 shows a section view of one integrated electronic atomizer of the present invention with the second electric connector being of the screw thread type. The electronic atomizer includes an atomizer tube 263 and, inside the atomizer tube 263, a second electric connector 267 with an internal screw thread with a rush pith 11 surrounded by a silica-gel insulator 18, supporting piece 268, heat equalizer 269 twined with electric heating wire 265, liquid container 261 inside which liquid-storing media 264 being filled with liquids is inserted, and an atomizer cap 262 with an air-puffing hole in the center. Between the liquid container 261 and the liquid media 264 there preferably is a side-space 290 (FIG. 3) for airflow. The second electric connector 267 may be inserted inside the atomizer tube 264.

The atomizer tube 263 is preferably made of a metallic or plastic material. The liquid-storing media 264 is preferably made of specially-designed cotton, while the supporting piece 268 is preferably made of a ceramic or plastic material in the shape of a cylinder or another configuration, which may be able to sustain a high temperature up to 1000 degrees centigrade. The heat equalizer 269 is preferably made of a special fiber which can withstand temperature as high as 2000 degrees centigrade. The electric heating wire 265 twined on the heat equalizer 269 can be made from tungsten or another electric heating material, which produces heat when the electric current flows therethrough. The two ends of the electric heating wire 265 are going through the small holes of the supporting piece 268 and connected to the second electric connector 267 to supply heat for atomization or vaporization of the liquid inside the liquid-storing media 264.

Figure 3:
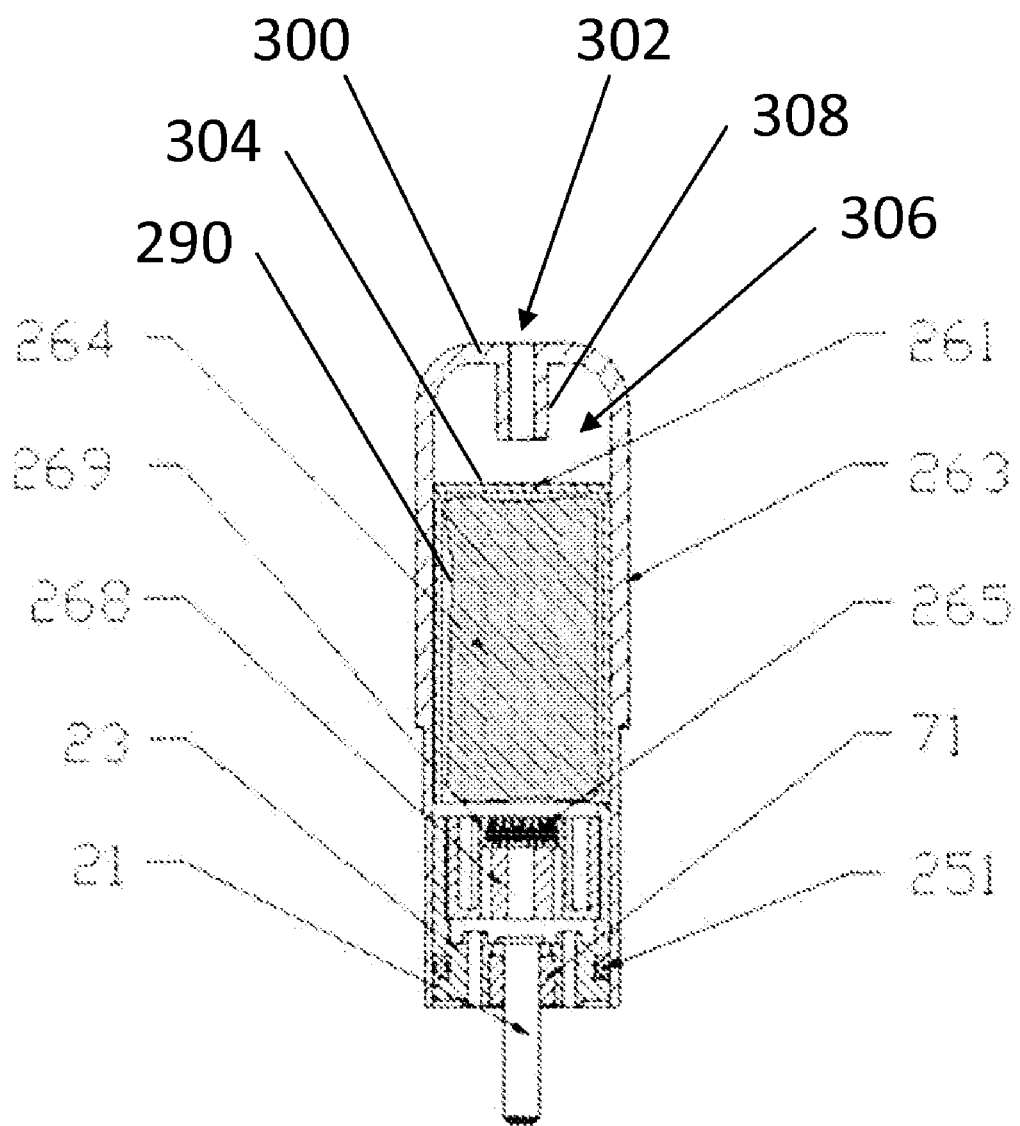
FIG. 3 is a section view of another integrated electronic atomizer of the present invention.

FIG. 3 is a section view of another integrated electronic atomizer with the second electric connector 21 being of a DC plug-socket type. The electronic atomizer includes an atomizer tube 263 and, inside the atomizer tube 263, a second electric connector comprised of a DC plug 21 located on a plug seat 71, leak-proof piece 23, seal washer 251, supporting piece 268, heat equalizer 269 twined with an electric heating wire 265, liquid container 261 inside which liquid-storing media 264 being filled with liquids is inserted, and an air-puffing hole in the center of one end of the atomizer tube 263. In FIG. 3, the air-puffing hole is placed atop the atomizer tube 263.

Figure 4:
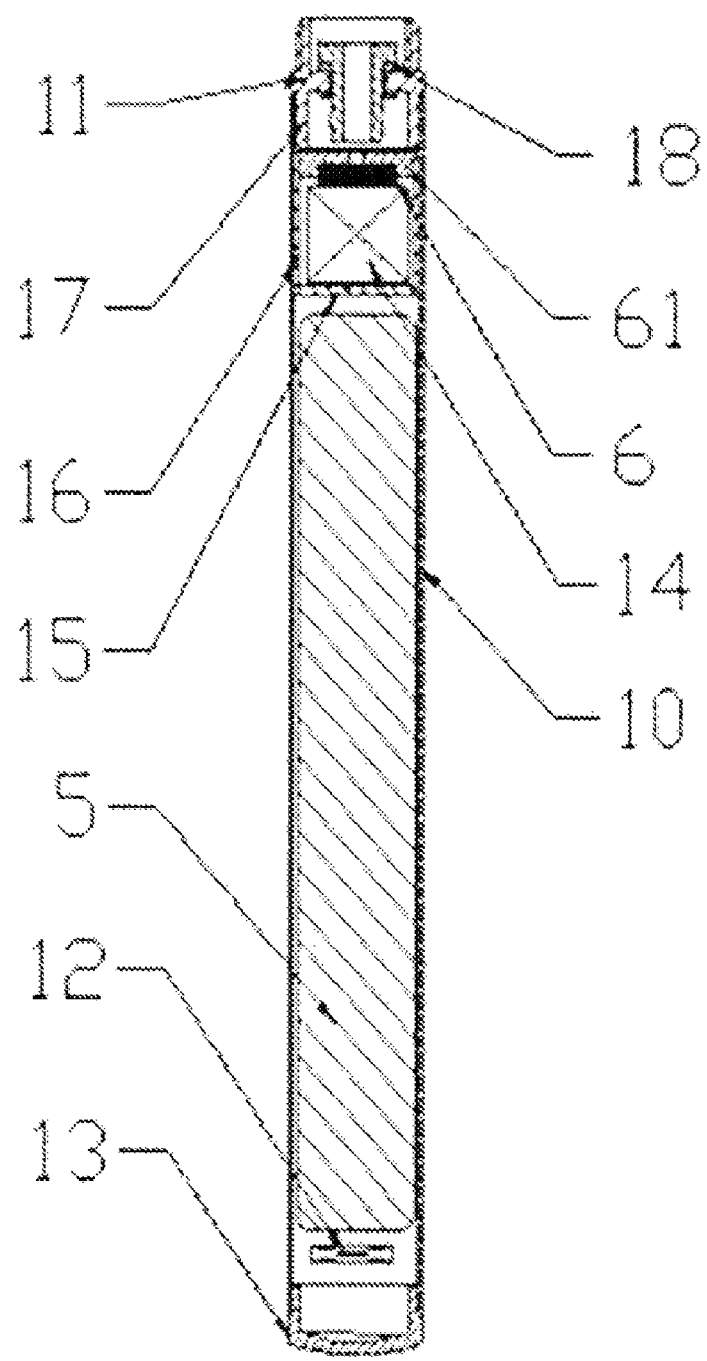
FIG. 4 is a section view of an electronic inhaler of the present invention.

FIG. 4 is a section view of one electronic inhaler having a first electric connector of a screw thread type. The electronic inhaler includes an inhaler tube 10, cigarette cap 13 with small holes for air inflow, LED indicator 12, electric power source 5, annular tube 16 with its cap 15, integrated circuit board with a CPU processor 14, electric airflow sensor 6, sensor supporter 61, and first electric connector 17 with an inserted rush pith 11 surrounded by a silica-gel insulator 18.

The electric power source 5 connects to the circuit board 14, which connects to the first electric connector 17 and the electric airflow sensor 6. The LED 12 is connected to both electric power source 5 and the circuit board 14. The electric airflow sensor 6 is assembled onto the sensor supporter 61. The first electric connector 17 with an outskirt screw thread is partially embedded in the inhaler tube 10, which can be connected to the second electric connector of the electric atomizer to form an electronic cigarette.

The inhaler tube 10 is made of either a metal or a plastic. The electric power source 5 may be a battery of rechargeable or non-rechargeable type. The first electric connector is generally made of copper or another metal conductor.

Figure 5:
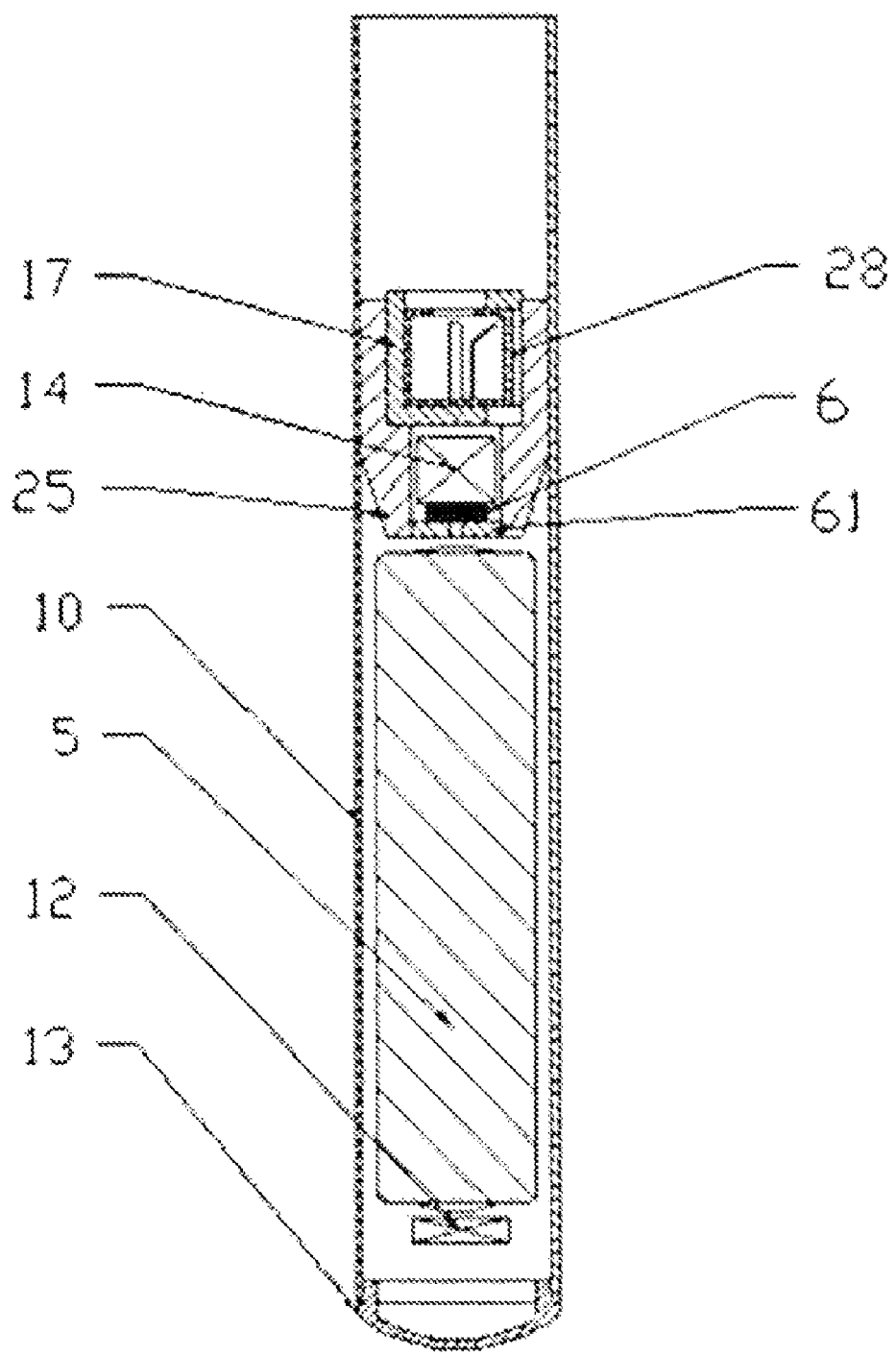
FIG. 5 is a section view of another electronic inhaler of the present invention.

FIG. 5 is a section view of another electronic inhaler having a first electric connector 17 of a DC plug-socket type. The electronic inhaler includes an inhaler tube 10, cigarette cap 13 with small holes for air inflow, LED indicator 12, electric power source 5, seal piece 25, sensor supporter 61, electric airflow sensor 6, integrated circuit board with a CPU processor 14, and the first electric connector 17 located on the DC socket seat 28.

The electric power source 5 connects to the circuit board 14, which connects to the first electric connector 17 and the electric airflow sensor 6. The LED 12 is connected to both electric power source 5 and the circuit board 14. The electric airflow sensor 6 is assembled onto the sensor supporter 61. The first electric connector 17 with the socket seat 28 is completely embedded in the inhaler tube 10, which can be connected to the second electric connector of the electric atomizer to form an electronic cigarette.

The inhaler tube 10 is made of either a metal or a plastic. The electric power source 5 may be a battery of rechargeable or non-rechargeable type. The first electric connector is generally made of copper or another metal conductor.

Figure 6:
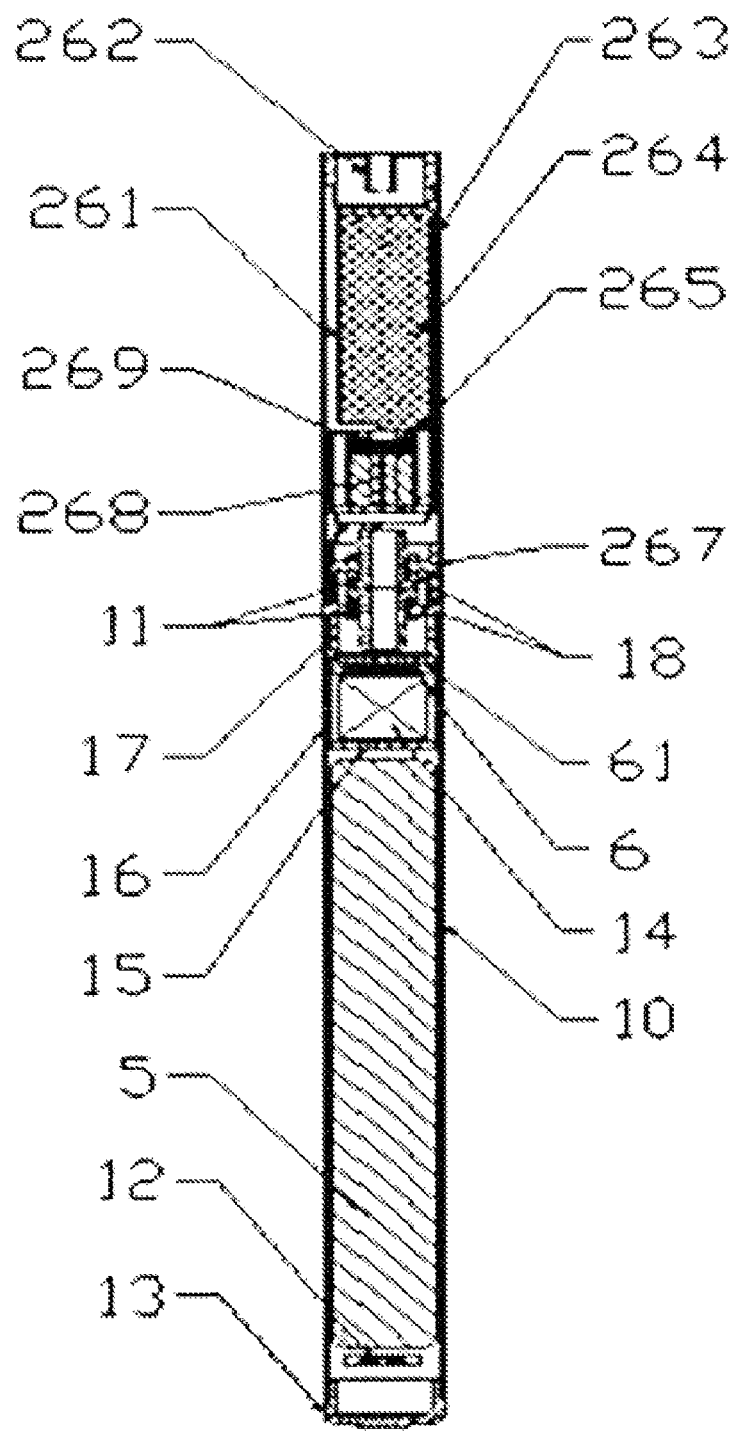
FIG. 6 is a section view of an electronic cigarette of the present invention.

FIG. 6 is a section view of one electronic cigarette when the electronic inhaler and electronic atomizer are connected via their respective electric connectors of the screw thread type. The electronic inhaler and the integrated electronic atomizer are fit together through their connectors of the same type to form the electronic cigarette. The connection is done via the first electric connector 17 of the electronic inhaler and the second electric connector 267 of the integrated electronic atomizer. The connection achieves the electric combination of the inhaler tube and the atomizer tube, each of which has a circular cross section in this embodiment, wherein the diameter is the inhaler is the same as or similar to that of the atomize. The user puffs on the end of the electronic cigarette with the air-puffing hole to activate the CPU processor through detection of an airflow signal and generate an electric current flowing through the electric heating wire, which achieves vaporization of the solution inside the liquid container.

Figure 7:
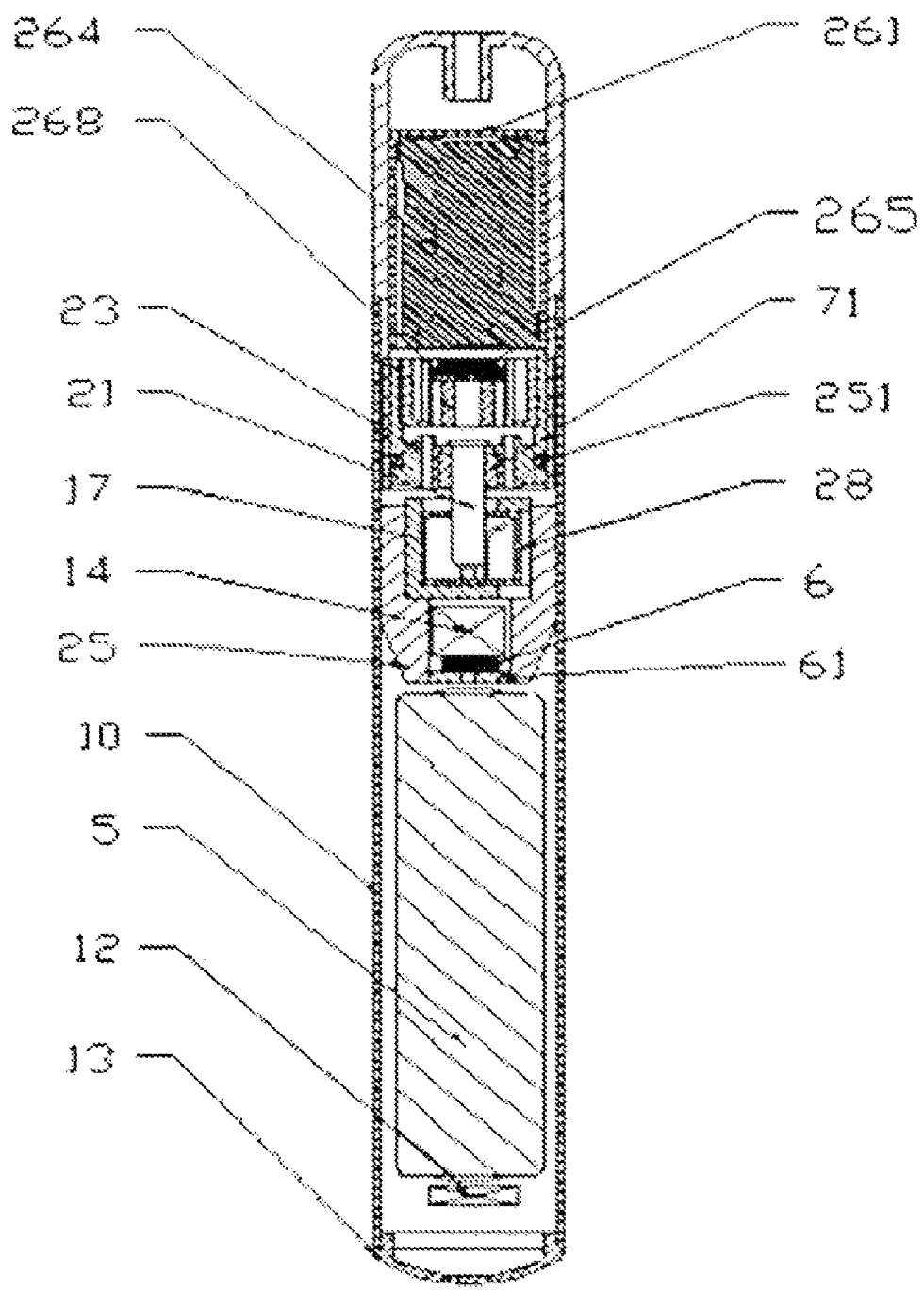
FIG. 7 is a section view of another electronic cigarette of the present invention.

FIG. 7 is a section view of another electronic cigarette when the electronic inhaler and electronic atomizer are connected via the electric connectors of the DC plug-socket type. The electronic inhaler and the integrated electronic atomizer are fit together through their connectors of the same type to form the electronic cigarette. The connection is done through the first electric connector socket 28 of the electronic inhaler and the second electric connector plug 21 of the integrated electronic atomizer. The connection achieves the electric combination of the inhaler tube and the atomizer tube, each of which has a circular cross section in this embodiment, wherein the diameter is the inhaler is the same as or similar to that of the atomizer. The user puffs on the end of the electronic cigarette with the air-puffing hole to activate the CPU processor through detection of an airflow signal and generate an electric current flowing through the electric heating wire, which achieves vaporization of the solution inside the liquid container.

Referring to FIGS. 2 and 3, the tubular electronic atomizer includes exterior wall 300 having air-puffing hole 302 formed therethrough. Liquid container 261 includes a container wall 304. Chamber 306 is disposed between exterior wall 300 and container wall 304. Tube 308 extends from air-puffing hole 302 and into chamber 306.

The invention claimed is:

1. An electronic cigarette comprising a tubular electronic inhaler and a tubular electronic atomizer that is detachably attached to the electronic inhaler, wherein the electronic inhaler includes an electric power source that provides an electric current to the electronic atomizer, and wherein the tubular electronic atomizer includes a container and media within the container, the media is soaked with a solution to be atomized, and between the container and the media there is a side-space for airflow tubular electronic, and wherein the tubular electronic inhaler includes an electric airflow sensor configured to turn on and off the electric power source by way of detecting an airflow, and the airflow sensor is a diaphragm microphone.

2. The electronic cigarette of claim 1, wherein the electronic inhaler includes a first electric connector disposed at a second end of the electronic inhaler, wherein the electronic atomizer includes a second electric connector disposed at a first end of the electronic atomizer, and wherein the first electric connector is connected to the second electric connector so that the electronic inhaler and the electronic atomizer form the electronic cigarette.

3. The electronic cigarette of claim 1, wherein the liquid container prevents or reduces liquid leak and reverse flow.

4. The electronic cigarette of claim 3, wherein the electronic atomizer includes an electric heating wire which generates heat for atomization of the solution soaked in the media inside the liquid container, a heat equalizer onto which the electric heating wire is wired and is made of fibers that can withstand a temperature up to 2000 degrees centigrade, wherein the heat equalizer ensures that the heat generated by the electric wire is uniform, and a supporting piece that is disposed next to the heat equalizer and is made of a plastic or ceramic material that can withstand a temperature up to 2000 degrees centigrade.

5. The electronic cigarette of claim 4, wherein the electronic atomizer includes a leak-proof member, wherein the leak-proof member and a second electric connector are closer to the first end of the electronic atomizer than the heat equalizer.

6. The electronic cigarette of claim 5, where the first electric connector is a DC socket and the second electric connector is a DC plug, wherein the DC plug is embedded onto the leak-proof piece through a plug seat, which is connected to the electric heating wire, and wherein the first end of the electronic atomizer is connected to the second of the electronic inhaler by placing the DC plug to the DC socket.

7. The electronic cigarette of claim 6, wherein the first electric connector is a cylinder terminal, and its outskirt is tightly embedded into the second end of the electric inhaler tube and its exposed portion has a screw thread, wherein the second electric connector is a cylinder terminal, which is tightly embedded into the first end of the electronic atomizer and has a screw thread inside the inhaler tube, and wherein the first electric connector and second electric connector are connected through the screw threads.

8. The electronic cigarette of claim 1, wherein the electronic atomizer includes, in sequence, a second electric connector, a leak-proof piece, a supporting piece, a heat equalizer coupled with an electric heating wire, the container filled with the media, and an atomizer cap with an air-puffing hole.

9. The electronic cigarette of claim 1, wherein the electric power source is inside the electronic inhaler.

10. The electronic cigarette of claim 1, wherein the tubular electronic atomizer includes an exterior wall having an air-puffing hole formed therethrough, wherein the liquid container includes a container wall, there being a chamber disposed between the exterior wall and the container wall, and wherein the tubular electronic atomizer includes a tube extending from the air-puffing hole and into the chamber.

11. The electronic cigarette of claim 1, wherein the media comprises cotton.

12. An electronic cigarette comprising a tubular electronic inhaler and a tubular electronic atomizer, wherein the electronic inhaler includes an electric power source that provides an electric current to the electronic atomizer, the electronic cigarette further comprising an integrated circuit board that has a Single Chip Micyoco that controls atomization of a liquid solution.

13. An electronic cigarette comprising a tubular electronic inhaler and a tubular electronic atomizer, wherein the electronic inhaler includes an electric power source that provides an electric current to the electronic atomizer, the electronic cigarette further comprising an electric airflow sensor that is used to turn on and off the electric power source by way of detecting an airflow and sending a signal to a Single Chip Micyoco, wherein the Single Chip Micyoco receives the signal from the electric airflow sensor, instructs the electric power source to send an electric current to the electronic atomizer, and a time period and a magnitude of the electric current.

14. The electronic cigarette of claim 13, wherein the electric airflow sensor is a diaphragm microphone.

15. The electronic cigarette of claim 13, further comprising an LED indicator inside the electronic inhaler, wherein the LED indicator is connected to the Single Chip Micyoco and the electric power source, and wherein the on time of the LED indicator is controlled by the Single Chip Micyoco.

16. An electronic cigarette comprising a tubular electronic inhaler and a tubular electronic atomizer, wherein the electronic inhaler includes an electric power source that provides an electric current to the electronic atomizer, wherein the electronic inhaler includes, sequentially from a first end of the electronic inhaler to the second end, a cigarette cap, an LED indicator, the electric power source, an electric airflow sensor, a circuit board for a Single Chip Micyoco, and a first electric connector.

17. An electronic cigarette comprising:
a tubular electronic inhaler; and
a tubular electronic atomizer that is detachably attached to the electronic inhaler,
wherein the electronic inhaler includes an electric power source that provides an electric current to the electronic atomizer,
wherein the tubular electronic atomizer includes a container and media within the container, the media is soaked with a solution to be atomized,
wherein the tubular electronic atomizer includes an exterior wall having an air-puffing hole formed therethrough, wherein the liquid container includes a container wall, there being a chamber disposed between the exterior wall and the container wall,
wherein the tubular electronic atomizer includes a tube extending from the air-puffing hole and into the chamber, and
wherein the tubular electronic inhaler includes an electric airflow sensor configured to turn on and off the electric power source by way of detecting an airflow, and the airflow sensor is a diaphragm microphone.

18. The electronic cigarette of claim 17, wherein the tubular electronic atomizer includes, in sequence, an electric connector, a leak-proof piece, a supporting piece, a heat equalizer coupled with an electric heating wire, the container filled with the media, and the air-puffing hole.

\* \* \* \* \*

UNITED STATES PATENT AND TRADEMARK OFFICE
CERTIFICATE OF CORRECTION

| | |
|---|---|
| PATENT NO. | : 8,205,622 B2 |
| APPLICATION NO. | : 12/437511 |
| DATED | : June 26, 2012 |
| INVENTOR(S) | : Guocheng Pan |

Page 1 of 1

It is certified that error appears in the above-identified patent and that said Letters Patent is hereby corrected as shown below:

In the Claims

Column 6, Line 34 should read:
side-space for airflow, and wherein the

Signed and Sealed this
Tenth Day of December, 2019

Andrei Iancu
*Director of the United States Patent and Trademark Office*

Disclaimer

8,205,622 B2 - Guocheng Pan, Cupertino, CA (US). ELECTRONIC CIGARETTE, CA (US). Patent dated June 26, 2012. Disclaimer filed October 27, 2023, by the assignee, VPR Brands, LP.

I hereby disclaim the following complete Claims 12, 16, 17 and 18 of said patent.

*(Official Gazette, December 19, 2023)*